United States Patent [19]
Amshey, Jr. et al.

[11] Patent Number: 6,060,260
[45] Date of Patent: May 9, 2000

[54] METHODS FOR REDUCING ADSORPTION IN AN ASSAY

[75] Inventors: Joseph W. Amshey, Jr., Mountain View; Rosy Sheng Donn, Saratoga, both of Calif.

[73] Assignee: Dade Behring Inc., Deerfield, Ill.

[21] Appl. No.: 09/032,626

[22] Filed: Feb. 27, 1998

[51] Int. Cl.$^7$ .................. G01N 33/552; G01N 33/545
[52] U.S. Cl. .................. 435/7.93; 435/962; 436/527; 436/531; 436/544; 436/546; 436/815; 436/825
[58] Field of Search .................. 435/7.93, 9.62; 436/527, 544, 546, 531, 815, 825

[56] References Cited

U.S. PATENT DOCUMENTS

| | | | |
|---|---|---|---|
| 3,817,837 | 6/1974 | Rubenstein et al. | 195/103.5 |
| 3,850,752 | 11/1974 | Schuurs et al. | 195/103.5 |
| 4,174,384 | 11/1979 | Ullman et al. | 424/8 |
| 4,220,450 | 9/1980 | Maggio | 23/230 |
| 4,220,722 | 9/1980 | Rowley et al. | 435/188 |
| 4,328,311 | 5/1982 | Rowley et al. | 435/188 |
| 4,816,391 | 3/1989 | Khanna | 435/7 |

OTHER PUBLICATIONS

M.J. Levy and A.P. Jaklitsch (1993) "Homogenous Enzyme Immunoassays: EMIT©" in *Diagnostics in the Year 2000 Antibody, Biosensor, and Nucleic Acid Technologies,* (Singh, P. et al. Eds.) Van Nostrand Reinhold, New York and references cited therein.

Syva Co. revised Jun. 1995 product data describing cassette instructions for use with EMIT© gentamicin assay.

*Primary Examiner*—Mary E. Ceperley
*Attorney, Agent, or Firm*—Linda M. Buckley; Robert L. Buchanan

[57] ABSTRACT

The present invention relates to methods for substantially reducing adsorption of at least one positively charged molecule to a negatively charged surface upon contact therebetween, the method comprising combining the positively charged molecule with at least one blocking agent in an amount sufficient to substantially reduce the adsorption of the positively charged molecule to the negatively charged surface.

38 Claims, No Drawings

METHODS FOR REDUCING ADSORPTION IN AN ASSAY

FIELD OF INVENTION

The present invention relates to methods for substantially reducing or eliminating adsorption of one or more positively charged molecules to a negatively charged surface. The methods of the invention have a variety of uses including substantially reducing adsorption of an aminoglycoside to a negatively charged surface in an analytical process.

BACKGROUND OF THE INVENTION

Assays for detecting positively charged molecules can be adversely impacted by adsorption (retention) of those molecules to a negatively charged surface such as those often present during an analytical assay. Such adsorption can substantially decrease sensitivity and reproducibility of the assay, thereby making the assay less accurate and less useful.

Aminoglycosides are one class of positively charged molecules that adsorb to a negatively charged surface. More particularly, the aminoglycosides can be adsorbed to glass vessels (e.g., cuvettes), tubing, and the like which are often components of commercial autoanalyzers. Adsorption of the aminoglycosides to such surfaces will reduce or eliminate presence of the aminoglycoside in a sample, thus interfering with the assay. Analysis of samples comprising trace quantities of certain aminoglycosides is particularly affected by the adsorption.

Accurate detection of positively charged molecules, such as aminoglycosides, is important in several respects. For example, it is often desirable to know how much of a therapeutic aminoglycoside is present in a biological sample, such as a fluid sample obtained from a patient. Specific assays for detecting therapeutic aminoglycosides and other positively charged molecules are known. For example, homogenous enzyme immunoassays such as EMIT® have been used to detect gentamicin, netilmicin, tobramycin, vancomycin and other therapeutics. See generally Levy, M. J. and A. P. Jaklitsch (1993) *Homogenous Enzyme Immunoassays: EMIT®* in *Diagnostics in the Year 2000 Antibody, Biosensor, and Nucleic Acid Technologies* (Singh, P. et al. Eds.) Van Nostrand Reinhold, New York and references cited therein.

U.S. Pat. No. 4,220,722 ('722 patent) and U.S. Pat. No. 4,328,311 ('311 patent) each disclose certain enzyme conjugates of aminoglycosides and their use in immunoassays.

U.S. Pat. No. 4,816,391 ('391 patent) discloses use of polyamines that are reported to decrease or prevent adsorption of aminoglycosides to glass surfaces. The polyamines are reported to include amino-substituted dextran, polyethylene amine, and large polymeric amines such as polybrene polyethylene polyamine (sometimes referred to as Polybrene®).

However, use of polyamines to decrease adsorption of positively charged molecules such as aminoglycosides has significant shortcomings. For example, use of large polymeric amines can complicate steps to remove same from many glass surfaces. Further, there is recognition that use of certain large polymeric amines such as Polybrene® can complicate assays such as immunoassays. In particular, there is recognition that Polybrene® is difficult to remove from glass cuvettes present in most autoanalyzers. This difficulty has contributed to poor precision and inaccurate results in many instances. More specifically, glass cuvettes that have been exposed to Polybrene®-containing calibrators behave differently from those which are not exposed. This problem can increase cost and labor associated with performing the analysis.

Accordingly, effective methods for substantially reducing or eliminating adsorption of positively charged molecules to negatively charged surfaces are desired. Particularly desired is effective methods for substantially reducing adsorption of aminoglycosides to the negatively charged surfaces such as glass and plastic.

SUMMARY OF THE INVENTION

The present invention relates to methods for substantially reducing or eliminating adsorption of at least one positively charged molecule to a negatively charged surface upon contact therebetween. In general, the methods include combining the positively charged molecule with at least one blocking compound in an amount sufficient to substantially reduce the adsorption of the positively charged molecules to the negatively charged surface. The methods of the present invention have a variety of applications, e.g., substantially reducing or eliminating adsorption of one or more aminoglycosides to a negatively charged surface in an analytical implementation.

We have found that adsorption of positively charged molecules to a negatively charged surface can be substantially reduced or eliminated by adding at least one blocking agent to the positively charged molecule. The blocking agents are used to effectively reduce adsorption (sometimes called "sticking") of the positively charged molecules to negatively charged surfaces. Importantly, the blocking agents can be readily washed-off the negatively charged surface unlike many prior polyamines. Accordingly, the present invention improves assays for detecting positively charged molecules that may contact glass, plastic or other negatively charged surfaces.

In one embodiment of the present invention, the method includes treating with at least one blocking agent in which the treating includes combining at least one of the positively charged molecules with at least one blocking agent prior to contact with the negatively charged surface. In another embodiment, the positively charged molecules and the negatively charged surface are treated with the at least one blocking agent, e.g., substantially simultaneously.

The methods of the present invention can be used to substantially reduce or prevent adsorption of a variety of positively charged molecules to a negatively charged surface. One such class of positively charged molecules exhibits a net positive charge at about neutral pH in an aqueous buffer. The method is particularly useful for molecules having a positive charge between from about 2 to about 4 and a molecular weight between from about 200 to about 1000, typically about 200 to about 750. The method of the present invention is also useful to reduce adsorption of positively charged molecules having a ratio of positive charge to molecular weight of between about 0.001 to 0.5 at about neutral pH. Illustrative are positively charged molecules having a net positive charge of about 3, preferably 3, and a molecular weight of between about 350 to 550, preferably about 450, such as certain aminoglycosides disclosed below.

The methods of the present invention are useful for substantially reducing or eliminating adsorption of positively charged molecules to a variety of negatively charged surfaces. For example, in one embodiment, the present methods are used to substantially reduce or eliminate adsorption to a negatively charged surface comprising one or more negatively charged groups preferably at about neutral pH. For example, the groups can include well-known charged groups such as —Si—O⁻, —COO⁻, or a —SO$_4^{-2}$. Such groups are found on a variety of negatively charged surfaces such as those comprising or consisting of glass or a plastic. Illustrative plastic surfaces include those comprising or consisting of particulate polymeric surfaces (e.g., beads) and particularly latex.

A variety of suitable blocking agents can be used in the present invention. In general, suitable blocking agents are those which are compatible with a biological assay, e.g., an immunological assay such as those described below. Preferred blocking agents are water soluble and are capable of reducing the adsorption of one or more positively charged molecules by between about 10% to 95% or more as determined by any of the standard adsorption assays which follow. Additionally, preferred blocking agents are substantially odorless, non-volatile and resistant to spontaneous oxidation. Additionally preferred blocking agents exhibit a net positive charge over a wide pH range (e.g., pH 5 to 9). Additionally, preferred blocking agents are capable of being washed from a negatively charged surface by contact with a suitable aqueous solvent or buffer, e.g., water. Illustrative of such blocking agents are specified quaternary ammonium compounds disclosed below.

Preferred quaternary ammonium compounds are generally quaternary ammonium salts. A suitable quaternary ammonium salt is typically a halide salt although other salts can be used depending on intended use. More particularly, the quaternary ammonium salt can be a tetramethyl ammonium, tetraethyl ammonium, tetrapropylammonium, trimethylethyl ammonium, or a triethylpropyl ammonium salt. In addition, the quaternary ammonium salt can be a N,N-trimethyl-N-dimethyl-bishexamethylene-triammonium, ethylenebis(trimethylammonium), propylenebis(trimethylammonium), butylenebis (trimethylammonium) pentamethylenebis (timethylammonium), heptamethylenebis (trimethylammonium) or a choline salt. In a preferred embodiment, the quaternary ammonium salt is a hexamethonium halide salt comprising at least one halide, e.g., hexamethonium bromide (HMB).

As noted, the present invention can be used to augment efficient analysis of a variety of positively charged molecules. For example, in one aspect, the invention can be used to substantially reduce or eliminate adsorption of at least one aminoglycoside to a negatively charged surface such as glass or plastic. In this aspect, the method can include combining the aminoglycosides with at least one suitable blocking agent typically in an amount sufficient to substantially reduce the adsorption by between about 10% to about 95% or more, preferably, about 50%, 60%, 70%, 80% to about 99% or more, as determined by any of the standard adsorption assays described below.

More particularly, when the method is used to substantially reduce or eliminate adsorption of at least one aminoglycoside in an assay, the aminoglycosides can be present (or suspected of being present) in a sample to be tested. In most cases, that sample will be a biological sample such as a fluid obtained from a subject, e.g., a human patient or domesticated animal such as dog, cat, or certain livestock. Illustrative fluids are serum, cerebrospinal fluid, saliva, urine, semen, vaginal secretions, ocular fluids and the like.

The present invention is particularly useful for improving what is sometimes referred to as a competitive assay or like term. Competitive assays are often used in the field to measure an amount of at least one positively charged molecule. Typically, one of such molecules is assayed. The present invention can improve such competitive assays by substantially reducing or eliminating adsorption of the positively charged molecule to a negatively charged surface (e.g., a glass vessel) in the assay. For example, in a particular application of the present invention, the competitive assay is improved by combining (i.e., adding) one or more suitable blocking agents to at least one assay component prior to contacting the negatively charged surface in the assay. Sometimes it will be useful to add the blocking agents to all or substantially all of the assay components. Such addition can be accomplished by a variety of means, including mixing the blocking agents with at least one of the assay components, preferably substantially all of the assay components prior to adding same to the negatively charged surface.

In a preferred embodiment, the addition is performed substantially simultaneously with addition of a sample to the negatively charged surface, which sample includes the positively charged molecule to be assayed. Combination of the blocking agents to the assay components can be performed by other strategies if desired. However, treatment of the negatively charged surface with the blocking agents prior to addition of the assay components, the sample, or both is preferably avoided for most applications. In another embodiment, the assay components, the sample, and the negatively charged surface are treated substantially simultaneously with at least one of the blocking agents prior to addition to the negatively charged surface. The amount of the blocking agents to be added will vary depending on intended use but will generally be between about 0.01% to about 10% (w/v) in the assay with between about 0.1% to about 0.5% (w/v) in the assay being preferred for many applications.

The improved competitive assay can be preformed by one or a combination of strategies. For example, in one approach, the assay can be conducted with a sample of interest and desired assay components to determine the presence or concentration, if desired, of at least one aminoglycoside (i.e., analyte) in the sample. Typically, this is achieved by mixing the sample together with a conjugate together with an antibody capable of specifically binding the aminoglycoside. In this embodiment, response of the analytical system to the presence of sample and the analyte therein, if present, and the response of the analytical system to a control or calibrator are usually measured separately. One suitable control is what is sometimes referred to in the field as a calibrator (or calibrators). Additionally, the conjugate is typically provided as the aminoglycoside covalently linked to one or more signaling molecules, usually one signaling molecule. In this example, the aminoglycoside, if present in the sample, is measured by detecting, and quantitating if desired, the extent of binding to the antibody capable of specifically binding the aminoglycoside. The sample aminoglycoside and the aminoglycoside linked to the signaling molecule compete for binding to the antibody. That competition can be related to the concentration of the sample aminoglycoside, if present, by one or a combination of conventional methods. Preferred blocking agents do not hinder that competition in the assay.

In one particular aspect of the assay, the assay components include the antibody, a tracer, i.e., a conjugate of the aminoglycoside covalently linked to signaling molecule and one or more reagents to help detect the signaling molecule. A variety of signaling molecules are known in the field including recognized fluorophores or a chemiluminescent molecules, e.g., fluorescein or FITC. In particular embodiments, the signaling molecule is a molecule capable of generating a detectable signal (e.g., by absorbance, fluorescence or phosphorescence) such as an enzyme capable of generating a detectable molecule. In this example, at least one of the blocking agents is a specified quaternary ammonium salt, preferably a quaternary ammonium halide salt. The quaternary ammonium salt is typically provided in an amount sufficient to substantially reduce or eliminate adsorption of the aminoglycoside in the sample, the assay components and the calibrator. The competitive assay is thus improved by reduction or elimination of the adsorption to negatively charged surfaces in the assay.

In a preferred embodiment, at least one of the assay components include a hexamethonium salt, preferably a hexamethonium halide salt comprising at least one halide, e.g., hexamethonium bromide (HMB). The HMB can be provided as a solid in an amount sufficient to provide between about 0.01% to 10% (w/v), preferably between about 0.1% to 5% (w/v) in the assay. It is often preferred that the hexamethonium salt be provided pre-mixed with one or all of the assay components.

In another embodiment of the assay, there is provided a method for detecting presence of one or more aminoglycosides in a vessel comprising a negatively charged surface, the method comprising the steps of combining a hexamethonium halide salt with at least one assay component, preferably substantially all of the assay components, and adding the assay components to the vessel in an amount sufficient to substantially reduce or eliminate adsorption of aminoglycosides present in subsequently added assay components, sample and/or calibrator. As noted previously, the calibrator and the sample are usually analyzed separately. In a particular embodiment, the vessel is one component of an analytical implementation such as an autoanlyzer.

In one embodiment, the improved competitive assay is used to detect the aminoglycosides. The assay can include an aminoglycoside calibrator (or multiple aminoglycoside calibrators), a signaling molecule comprising the aminoglycoside covalently linked to an enzyme, and a monoclonal antibody capable of specifically binding the aminoglycoside. The signaling molecule and the antibody can be provided in any acceptable format although solutions or lyophilized components will usually be desirable. Combination of one or all of the assay components with the hexamethonium halide salt (i.e., adding the salt thereto) will substantially reduce or eliminate adsorption of the aminoglycoside to negatively charged surfaces in the vessels, e.g., glass or plastic cuvettes, tubing, and the like. In a preferred embodiment, the hexamethonium halide salt is hexamethonium bromide (HMB) provided in an amount sufficient to provide between about 0.01% to 10% (w/v), preferably about 0.1% to 5% (w/v) in the assay.

In a particular embodiment of the improved competitive assay, the aminoglycoside calibrator is a series of gentamicin calibrators each comprising a known amount of gentamicin, and the enzyme is a dehydrogenase such as glucose 6-phosphate dehydrogenase. The method typically further includes measuring absorbance of a detectable molecule produced by the enzyme such as reduced nicotinamide adenine dinucleotide (NADH) or like molecule known in the field.

In general, the methods of the present invention are compatible with analysis of a variety of aminoglycosides including therapeutic aminoglycosides such as gentamicin, netilmicin, tobramycin, vancomycin and amikacin. In embodiments in which an improved competitive assay is selected, that assay will include use of at least one blocking agent along with one or more calibrators, signaling molecules and antibodies selected in accordance with the aminoglycoside of interest. Preferably, the blocking agents are added to substantially all of the assay components although other treatment regimes can be conducted as provided herein.

Further provided by the present invention is a kit for detecting at least one aminoglycoside in a biological sample. In one embodiment, the kit includes a suitable calibrator (or more than one suitable calibrator) which calibrator includes one or more aqueous buffers comprising a known amount of the aminoglycoside to be tested, a conjugate (tracer) comprising a signaling molecule comprising glucose 6-phosphate dehydrogenase covalently linked to the aminoglycoside to be tested, an antibody (polyclonal or monoclonal) capable of specifically binding the aminoglycoside and a suitable quaternary ammonium salt for substantially reducing or eliminating adsorption of the aminoglycoside to negatively charged surfaces such as glass or plastic. Illustrative of such a quaternary ammonium salts are quaternary ammonium halide salts, preferably hexamethonium halide salts comprising at least one halide and more preferably hexamethonium bromide (HMB). Preferably the quaternary ammonium salt is pre-mixed with one or substantially all of the assay components in the kit.

In one embodiment of the kit, the aminoglycoside to be tested is gentamicin and the hexamethonium salt is hexamethonium bromide (HMB) preferably provided in an amount sufficient to provide about 0.01% to 10% (w/v) hexamethonium bromide (HMB) in an assay, preferably between about 0.1% to 0.5% (w/v) in the assay. The kit may further include at least one of an anti-microbial compound, a stabilizer, excipient or a preservative as needed.

DESCRIPTION OF THE INVENTION

As discussed above, the present invention relates to a method for substantially reducing or eliminating adsorption of at least one positively charged molecules to a negatively charged surface upon contact therebetween. The method generally includes treating with at least one blocking compound, preferably one blocking compound, in an amount sufficient to substantially reduce the adsorption of the positively charged molecules to the negatively charged surface. Illustrative positively charged molecule are aminoglycosides and particularly therapeutic aminoglycosides such as those disclosed herein.

In one aspect, the present invention relates to a method of diminishing retention of at least one aminoglycoside to a negatively charged surface (e.g., a glass surface). In one embodiment, the aminoglycoside is combined with at least one suitable blocking agent in an effective amount sufficient to substantially reduce or eliminate the adsorption without significant retention of the blocking agents thereon. For example, the blocking agent can be added to at least one assay component, control or a calibrator comprising the aminoglycoside of interest. In another example, at least one appropriate blocking agent is added to substantially all of the assay components, control or calibrator. Accordingly, one objective of the present invention is to substantially reduce or prevent such aminoglycoside adsorption, thereby enhancing performance of a variety of assays for detecting the aminoglycoside.

By the term "substantially reduce" or like term is meant decreasing adsorption of at least one positively charged molecule of interest, e.g., an aminoglycoside, by between about 10% to about 95% or more, more preferably at least about 50% up to 98% or more as determined by any of the standard adsorption assays described herein. Additionally, preferred blocking agents will decrease the adsorption by between about 50%, 60%, 70%, or about 80% to about 99% or more. As will become apparent from the discussion which follows, the substantial reduction in the adsorption is achieved by treatment with one or more suitable blocking agents in an amount sufficient to reduce the adsorption. A "calibrator" is herein to assure that on a daily basis the dose response curve is valid.

Methods for determining and quantitating positive charge of a desired molecule at about neutral pH are known in the field and can be performed by a variety of conventional methods. For example, one method is to determine ionization constants by monitoring pH while titrating with a suitable base or acid. A titration plot is typically produced. The positive charge on the molecule is identified, e.g., by presence of inflection points in a titration plot. Use of the Henderson-Hasselbach can identify the proportion of ionized and unionized form of the salt. Another method is to determine electrophoretic mobility of the molecule.

As noted, a variety of blocking agents can be used in accord with this invention. For example, in one embodiment, a suitable blocking agent is an alkylammonium salt represented by the following Formula I:

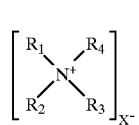

wherein, $R_1$, $R_2$, $R_3$, and $R_4$ are each independently a lower alkyl group, the same or different; and X is a counter-ion. In particular embodiments, the blocking agent is of a salt of tetramethyl ammonium, tetraethyl ammonium, tetrapropylammonium, trimethylethyl ammonium, and triethylpropyl ammonium.

A "salt" as defined herein can be an inorganic acid addition salt such as hydrochloride, hydrobromide, sulfate, sulfite, hemi-sulfate, phosphate, nitrate, and organic addition salts such as acetate, maleate, oxalate, fumarate, mesylate, etc. Preferred salts are quaternary ammonium salts, preferably quaternary ammonium halide salts comprising at least one halide such as those alkylammonium halide salts specified herein. Preferred salts include a single halide such as chlorine, bromine, or iodine.

By the term "counter-ion" is meant a negatively charged atom or molecule that is capable of forming an ionic bond in the salt. Illustrative counter-ions include halides such as chloride, fluoride, bromide and iodide.

By the term "lower alkyl" is meant a straight-chain or branched alkyl group comprising 1 to 6 carbons (inclusive). Illustrative alkyl groups include methyl, ethyl, propyl, butyl, pentyl, hexyl, isopropyl, isobutyl, tert-butyl, isohexyl, isopentyl and the like.

In another embodiment, a suitable blocking agent is an alkylammonium salt represented by the following Formula II:

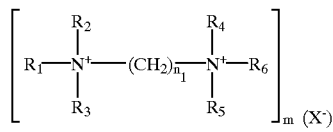

wherein, $R_1$, $R_2$, $R_3$, $R_4$, and $R_5$ are each independently a lower alkyl group; X is a counter-ion; $n_1$, $n_2$ are each independently 1 to 7 (inclusive), the same or different; and $R_6$ is a lower alkyl group and m is 2; or

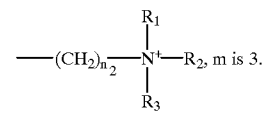

In particular embodiments, the blocking agent is a salt of N,N"-trimethyl-N'-dimethyl-bishexamethylene-triammonium, ethylenebis(trimethylammonium), propylenebis(trimethylammonium), butylenebis(trimethylammonium), pentamethylenebis(timethylammonium), and heptamethylenebis(trimethylammonium).

In another embodiment, a suitable blocking agent is an alkylammonium salt represented by the following Formula III:

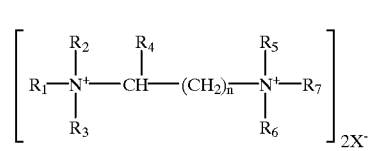

wherein, $R_1$, $R_2$, $R_3$, $R_5$, $R_6$, and $R_7$ are each independently lower alkyl, the same or different; $R_4$ is methyl, ethyl, propyl, or isopropyl; n is 1 to 7 (inclusive); and X is a counter-ion.

In another embodiment, a suitable blocking agent is an alkylammonium salt represented by the following Formula IV:

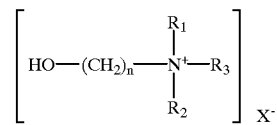

wherein, $R_1$, $R_2$, and $R_3$, are each independently lower alkyl, the same or different; n is 1 to 5 (inclusive); and X is a counter-ion. In one particular embodiment, the blocking agent is a choline salt.

In another embodiment of Formulae II and III above, at least one of the -R groups can be hydrogen provided that the represented compound includes at least one quaternary ammonium group. Preferably, one or two of such -R groups can be hydrogen in this example.

In another embodiment, a suitable blocking agent for use in accord with the present invention comprises about 1 monomeric unit of a polymeric amine, e.g., Polybrene®. Typically, that monomeric unit will exist as a salt such as a halide salt.

For example, in one embodiment the blocking agent is a hexamethonium salt represented by the following Formula V:

$$[(CH_3)_3N^+(CH_2)_6N^+(CH_3)_3]2X^- \qquad V$$

wherein X is a counter-ion. Illustrative are hexamethonium halide salts comprising one halide or more than one halide. For example, a preferred hexamethonium halide salt is hexamethonium bromide (HMB).

Preferred blocking agents as represented by Formulae I, II, III, IV and V above are capable of reducing adsorption of one or more desired positively charged molecules by between about 10% to about 95% or more as determined by any of the standard adsorption assays described below. Preferably, the adsorption is reduced by about 50% up to about 99% or more as determined in the assays. Additionally, preferred blocking agents decrease adsorption of the positively charged molecules by between about 50%, 60%, 70%, 80% up to about 98% or about 99% or more.

Blocking agents described herein can be obtained from a variety of commercial sources (e.g., Sigma Chemical Co., St. Louis, Mo.; Aldrich Chemical Co., Inc., Milwaukee, Wis.). Alternatively, the blocking agents can be made by synthetic or semi-synthetic routes well-known in the field. For example, in one approach, a desired blocking agent can be made by reacting a suitable alkyl halide, preferably an alkyl bromide or alkyl iodide, with an appropriate primary, secondary or tertiary amine. The blocking agent can be purified if desired by standard approaches.

As noted, at least one of the blocking agents, preferably all of the blocking agents including one blocking agent is provided in an amount sufficient to substantially reduce or eliminate adsorption of a positively charged molecule of interest such as an aminoglycoside. It is often preferred to provide the blocking agents in a solution, preferably pre-mixed with at least one of the assay components described above. In a particular embodiment, the blocking agents are provided pre-mixed with an antibody capable of specifically binding the aminoglycoside of interest, an aminoglycoside covalently linked to an enzyme (conjugate or tracer), and one or more reagents to help detect the conjugate. The blocking agents can be provided as a solid in some instances and it will be desirable to solublize that solid by addition of a suitable liquid such as water. Preferably if the blocking agent is provided as a solid it will be in an amount sufficient to provide between about 0.01% to 10% (w/v) or more of the blocking agent, preferably between about 0.5% to 5% (w/v) of the blocking agent in the assay.

More specifically, in one embodiment, novel formulations are provided involving combinations of aminoglycosides or derivatives thereof, hexamethonium bromide, and usually including various additives such as buffer, salt, proteins, stabilizers, or the like. In this embodiment, the presence of the hexamethonium bromide prevents the loss of active aminoglycoside, believed to be due to adsorption of the aminoglycoside to glass container walls. That is, the quantitation as determined by analytical methods such as immunoassays remains substantially constant over long periods of time in glass vessels. Also, on automated analyzers employing glass components such as reaction cuvettes, the novel methods of the present invention provide superior analyzer performance including precision and accuracy.

The aminoglycosides of interest may be the naturally-occurring aminoglycosides or modified aminoglycosides, particularly where one or more aminoglycosides are conjugated to a protein, e.g., an enzyme, or other label. The formulations are employed in immunoassays for the detection of the presence of an aminoglycoside, where the aminoglycoside is present as a compound of a sample to be analyzed or as a calibrator for establishing a standard. The formulations will vary depending upon whether the aminoglycoside is present conjugated to a label or unconjugated.

Illustrative aminoglycosides have been described in Levy, supra, and include therapeutic aminoglycosides such as tobramycin, gentamicin, kanamycin, amikacin, and vancomycin.

In embodiments of the present invention where a hexamethonium salt such as hexamethonium bromide is at least one of the blocking agents of choice, the blocking agent is added to or combined with the selected aminoglycoside in an effective amount sufficient to diminish the retention or adsorption or sticking of the aminoglycoside to a glass surface, whereby the aminoglycoside does not bind to such surface due to the binding of the hexamethonium bromide. Therefore, typically the glass surface will be washed whereby the aminoglycoside will be removed while at the same time, unlike polyamides, the hexamethonium salt will not be retained, i.e., it is removed from the glass surface.

The ratio of hexamethonium salt to the molecules of aminoglycosides will generally be in the range of about 5,000 to 70,000:1.

In one embodiment, formulations for use in this invention are conveniently provided as powder formulations to be reconstituted before use and to provide for stable responses upon long storage in glass. Formulations may also be prepared as stabilized liquids. For use in immunoassays, the formulations will usually provide for a number of materials, depending upon whether the formulation is to be used as a calibrator or is to serve as an active reagent, where the aminoglycoside is conjugated to a label. Immunoassay formulations may be packaged in more than one container such that the desired characteristics are achieved when the contents of the containers are mixed together with sample to perform the analysis. The hexamethonium salts may be provided in one or more of the containers so as to achieve the desired properties. For example, if the aminoglycoside is packaged in glass, it is desirable to have the hexamethonium salt present with the aminoglycoside. If the aminoglycoside is packaged in some other material such as plastic, where the aminoglycoside has less tendency to adsorb to the surfaces, the hexamethonium salts may be provided in other containers than the aminoglycoside providing that when the formulation components are mixed together to perform the analysis, the blocking agents (or blocking agent) are present in sufficient concentration to prevent adsorption of the aminoglycosides to glass components of the analyzer used to conduct the testing.

Where the aminoglycoside is to be used as a calibrator, its concentration in the formulation will vary in accordance with the desired concentration of the aminoglycoside in the calibrator solution upon reconstitution if the calibrator is provided in dried form. The amount of aminoglycoside will represent a value of interest related to the therapeutic dosage range of the particular aminoglycoside. Therefore, the particular amount of the aminoglycoside in the formulation is not usually critical, so long as the aminoglycoside formulation, if provided in dried form, can be readily reconstituted in an accurate and reproducible manner. Generally, the aminoglycoside will be present in 0.001 to 0.01 wt % of the powder formulation, more usually 0.002 to 0.01 wt %. This will provide a concentration upon reconstitution of about 1 to about 50 $\mu$M, preferably between about 2 to about 25 $\mu$M, more preferably between about 10 to about 22 $\mu$M.

Illustrative of calibrators will be compositions leaving between 99% and 99.9% dry weight of serum protein, which can be conveniently Freon treated and lyophilized. Included with the serum will be a stabilizer, e.g., thimerosal. In minor amount will be a sufficient amount of the aminoglycoside to provide for the desired concentration of the aminoglycoside upon reconstitution.

It will be appreciated that the precise concentration of the blocking agent selected is not important so long as the blocking agent is capable of reducing the adsorption by between about 10% to 99% as determined by any of the standard adsorption assays described below. Selection of an appropriate blocking agent or combination of blocking agents in accord with this invention will also be guided by desirable characteristics of the blocking agent such as water solubility, substantial lack of odor, non-volatility and resistance to spontaneous oxidation.

In embodiments of the present invention where the aminoglycoside is present as a conjugate reagent, the weight percent of the reagent will vary widely, depending upon the nature of the label, the protocol of the assay, the nature of the assay, the blended dilution, as well as other relevant factors. For enzyme labels, the concentration can be provided in the range of about 10 to 100 nM, while with fluorescent labels, the concentration will generally range from about 1 nM to 10 $\mu$M, more usually from 1 to 10 $\mu$M.

For a fluorescent reagent, the fluorescent reagent may be employed neat or may be combined with the above ingredient in the amounts indicated, or any one or more of the ingredients where the relative percentages would be modified accordingly.

Upon reconstitution, in most embodiments the buffer should provide a concentration of about 0.01% to about 10% (w/v) of the blocking agent or blocking agents selected. The pH should generally be in the range of about 5–9, more usually about 6.5–8.5 and including neutral pH. The appropriate pH will be selected for optimum stability of the label and the aminoglycoside, as well as for optimum assay performance. The inert protein concentration will generally be from about 0.1 to 90 wt %. The aminoglycoside concentration as conjugate will generally be in the range of about 0.1–50 nM.

In most instances, reconstitution when required will normally be achieved with water, usually distilled water, which may be subject to additional purification. Diluents appropriate to achieve the desired final formulation composition may also be provided in separate containers.

The reagents find us in a wide variety of immunoassays which are described in U.S. Pat. Nos. 3,817,837; 3,850,752; 4,174,384; 4,220,450; and the like.

The concentration of assay components such as antibodies, tracers, conjugates (labeled analyte) in a desired formulation can be optimized by methods known to those skilled in the art. Optimization is typically guided by a desired signal output or dose response curves. See e.g., Levy, M. J., supra; and Dade-Behring company literature cited herein for additional disclosure relating to these components.

A candidate blocking agent in accord with this invention can be tested for capacity to substantially reduce adsorption of a positively charged molecule by one or a combination of strategies. For example, in one approach sometimes referred to herein as a "standard adsorption assay", the anti-adsorption activity of the blocking agent is quantified by methods generally involving serial transfer. More particularly, the methods involve serial transfer of the positively charged molecule in vessels comprising negatively charged surfaces in which one set of vessels have been treated with the candidate blocking agent and another set has not been so treated (control). The extent of adsorption in the both sets of vessels can be quantitated by any acceptable means including those specified in the examples which follow. One specific approach includes one or more of the following steps:

a) preparing a solution of a positively charged molecule in a first vessel comprising a negatively charged surface which solution has been combined with the candidate blocking agent prior to contact with the first vessel, b) transferring a portion of the solution into another vessel comprising the negatively charged surface, c) repeating step b) for a number of times sufficient to adsorb the positively charged molecule to consecutive vessels comprising the negatively charged surface; and d) determining concentration of the positively charged molecule in the first vessel and the consecutive vessels.

In most cases, the standard adsorption assay will be performed with a suitable control which will be the same or closely related to steps a) through d) above but will not include addition of the candidate blocking agent. In most cases, step b) will be repeated about 2, 3, 4, 5, 6, 7 or more times up to about 10 times or more depending on the adsorption desired. The candidate blocking agent can be used in the assay in any acceptable amount including about 0.001% to about 10% (w/v) preferably about 0.01% to about 5% (w/v), and more preferably about 0.1% to about 5% (w/v) as needed. The extent of adsorption can be expressed in any acceptable format including the percent loss of the positively charged molecule in the serial transfer. As will be more appreciated by the examples which follow, loss of gentamicin in a tube is amplified by serial transfer in the absence of a suitable amount of hexamethonium bromide (HMB). Preferred blocking agents are readily washed-off from the vessels selected, e.g., with water or other suitable solvent.

The methods of the present invention can be used to substantially reduce or eliminate adsorption of a variety of positively charged molecules including aminoglycosides such as gentamicin. As noted, the methods of this invention can be used to improve competition assays and particularly immunological competitive assays formatted to detect gentamicin. Such assays can be conducted by several means including use of an autoanalyzer (e.g., a Syva®30R autoanalyzer). In this instance, the methods substantially reduce or eliminate sticking of gentamicin to negatively charged vessels in the autoanalyzer including glass or plastic surfaces.

The following examples are offered by way of illustration and not by way of limitation.

EXAMPLE 1

The following examples relate to EMIT® assays for detecting gentamicin. Additional disclosure relating to the assays can be found in Levy, supra and in literature supplied by commercial manufacturers such as Dade-Behring. See e.g., Syva Co. revised June 1995 product data describing cassette instructions for use with an EMIT® gentamicin assay.

The following experiments illustrate the blocking effect of HMB in reducing the adsorption of gentamicin to glass surface. This blocking function applies to both conjugated (i.e., gentamicin-enzyme conjugate) and unconjugated gentamicin (unlabeled gentamicin drug).

(1) Gentamicin Enzyme Conjugate Adsorption Study

In EMIT® assays, the enzymatic activity is measured by the rate of conversion of oxidized nicotinamide adenine dinucleotide (NAD) to reduced nicotinamide adenine dinucleotide (NADH), resulting in an absorbance (A) change that is measured spectrophotometrically at 340 nm. This enzymatic rate is expressed as "ΔmA/min", where ΔmA=ΔA×1000.

Gentamicin enzyme conjugate was added to three different aqueous formulations. Formulation A contained 0% HMB, Formulation B contained 0.1% by weight HMB and formulation C contained 0.5% by weight HMB. These three enzyme conjugate formulations were each initially prepared and stored in plastic tubes. The enzymatic activity was tested for each formulation as the original baseline rate. Thereafter each formulation was transferred to a glass tube and the tube was vortexed to ensure the contact between the aqueous formulation and the glass surface. A small sample was then taken out for measuring the enzymatic activity. The remaining conjugate solution was again transferred to a fresh glass tube. This transfer process was repeated four times to amplify the adsorption phenomenon. The enzymatic rate after each transfer process was compared to its original rate and the percent difference was calculated. The following table clearly indicates that HMB reduces the gentamicin enzyme conjugate adsorption to the glass surface.

Example 1:

| Enzymatic Rates (in ΔmA/min) and % Change to original | | | | | |
|---|---|---|---|---|---|
| | A (0% HMB) | | B (0.1% HMB) | | C (0.5% HMB) | |
| | Rates | % Change | Rates | % Change | Rates | % Change |
| Original (in plastic) | 156.5 | 0 | 156.8 | 0 | 156.4 | 0 |
| Glass transfer 1 | 150.9 | −3.6% | 153.5 | −2.1% | 155.3 | −0.7% |
| Glass transfer 2 | 134.9 | −13.8% | 143.1 | −8.7% | 150.8 | −3.5% |
| Glass transfer 3 | 121.0 | −22.7% | 132.4 | −15.6% | 142.3 | −9.0% |
| Glass transfer 4 | 108.7 | −30.6% | 123.3 | −21.4% | 140.1 | −10.4% |
| Glass transfer 5 | 80.8 | −48.4% | 105.9 | −32.5% | 124.7 | −20.2% |

EXAMPLE 2

The procedure of Example 1 was repeated except that a different substrate formulation was used when monitoring the enzymatic activity of the gentamicin enzyme conjugate. It contained 1% by weight Bovine Serum Albumin ("BSA") and 0.01% by weight of silicone. The results in the following table again indicate the blocking effect of HMB on Gentamicin conjugate to glass surfaces.

Example 2:

| Enzymatic Rates (in ΔmA/min) and % Change to original | | | | | |
|---|---|---|---|---|---|
| | A (0% HMB) | | B (0.1% HMB) | | C (0.5% HMB) | |
| | Rates | % Change | Rates | % Change | Rates | % Change |
| Original (in plastic) | 156.0 | 0 | 157.2 | 0 | 159.2 | 0 |
| Glass transfer 1 | 150.4 | −3.6% | 152.7 | −2.8% | 155.2 | −2.5% |
| Glass transfer 2 | 136.1 | −12.7% | 142.8 | −9.2% | 148.7 | −6.6% |
| Glass transfer 3 | 121.3 | −22.2% | 133.2 | −15.3% | 143.6 | −9.8% |
| Glass transfer 4 | 109.1 | −30.1% | 123.4 | −21.5% | 139.8 | −12.2% |
| Glass transfer 5 | 82.2 | −47.3% | 109.2 | −30.5% | 126.1 | −20.8% |

(2) Gentamicin Drug Adsorption Study

EXAMPLE 3

Using a standard immunoassay technique, the amount of gentamicin in a sample can be determined by reference to a standard curve generated with calibrator of known gentamicin concentration. Three aqueous formulations containing gentamicin drug at the target concentration of 7 μg/ml were prepared in plastic containers. Formulation D contained 0% by weight HMB, Formulation E contained 0.1% by weight HMB and Formulation F contained 0.5% by weight HMB. The original concentration for each formulation was determined using the established standard curve. The transfer process of Example 1 was carried out. After each transfer the amount of gentamicin drug in this solution was determined using the same established standard curve. The following table clearly indicates that HMB blocks the binding of gentamicin to glass surfaces.

Example 3

| Concentration (in μg/ml) and % Change to original | | | | | |
|---|---|---|---|---|---|
| | D (0% HMB) | | E (0.1% HMB) | | F (0.5% HMB) | |
| | Conc. | % Change | Conc. | % Change | Conc. | % Change |
| Original (in plastic) | 7.45 | 0 | 7.52 | 0 | 7.73 | 0 |
| Glass transfer 1 | 7.59 | 1.9% | 7.65 | 1.8% | 7.49 | −3.1% |
| Glass transfer 2 | 7.66 | 2.8% | 8.06 | 7.2% | 7.67 | −0.7% |
| Glass transfer 3 | 7.30 | 2.0% | 7.94 | 5.7% | 7.65 | −9.1% |
| Glass transfer 4 | 6.43 | −13.6% | 7.96 | 5.9% | 7.86 | 1.7% |
| Glass transfer 5 | 5.98 | −19.7% | 7.42 | −1.3% | 7.61 | −1.5% |

All references disclosed herein are incorporated by reference.

The invention has been described in detail with particular reference to the above embodiments. It will be understood, however, that variations and modifications can be effected within the spirit and scope of the invention.

What is claimed is:

1. A method for substantially reducing adsorption of at least one positively charged molecule to a negatively charged surface upon contact therebetween, the method comprising combining the positively charged molecule with at least one blocking agent in an amount sufficient to substantially reduce the adsorption of the positively charged molecule to the negatively charged surface, wherein at least one of the blocking agents comprises:

Formula I:

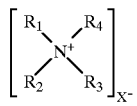

wherein $R_1$, $R_2$, $R_3$, and $R_4$ are each independently a lower alkyl group, the same or different; and X is a counter-ion;

Formula II:

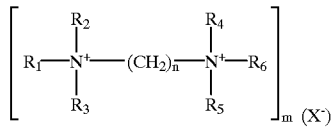

wherein, $R_1$, $R_2$, $R_3$, $R_4$, and $R_5$ are each independently a lower alkyl group, the same or different; X is a counter-ion, n is 1 to 7, the same or different; $R_6$ is a lower alkyl group and m is 2; or

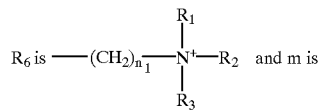

Formula III:

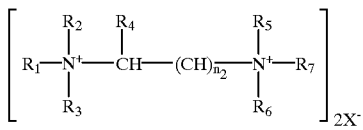

wherein, $R_1$, $R_2$, $R_3$, $R_5$, $R_6$, and $R_7$ are each independently lower alkyl, the same or different; $R_4$ is methyl, ethyl, propyl, or isopropyl; $n_1$ is 1 to 7; X is a counter-ion; and $n_2$ is 1 to 7; or Formula IV:

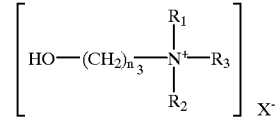

wherein, $R_1$, $R_2$, and $R_3$, are each independently lower alkyl, the same or different; $n_3$ is 1 to 5; and X is a counter-ion, and further wherein the positively charged molecule adsorbs to the negatively charged surface in the absence of the blocking agent.

2. The method of claim 1, wherein the method further comprises combining the positively charged molecule with the blocking agent prior to contact with the negatively charged surface.

3. The method of claim 1, wherein the method further comprises treating the negatively charged surface with the blocking agent prior to contacting the negatively charged surface with the positively charged molecule.

4. The method of claim 1, wherein the positively charged molecule has a ratio of positive charge to molecular weight of between about 0.001 to 0.1 at about neutral pH.

5. The method of claim 4, wherein the positive charge is between about 2 to about 4 and the molecular weight of the positively charged molecule is between about 200 and about 750.

6. The method of claim 5, wherein the positively charged molecule is an aminoglycoside.

7. The method of claim 1, wherein the negatively charged surface comprises at least one of a —Si—O$^-$, —COO$^-$, or a —SO$_4^{-2}$ group.

8. The method of claim 7, wherein the negatively charged surface is a glass or a plastic.

9. The method of claim 8, wherein the negatively charged surface is a particulate polymeric surface.

10. The method of claim 9, wherein the particulate polymeric surface comprises latex.

11. The method of claim 1, wherein the blocking agent reduces or eliminates the adsorption by between about 10% to about 99% as determined by a standard adsorption assay.

12. The method of claim 1, wherein the blocking agent comprises about 1 monomeric unit comprising between about 2 to about 20 carbons or more, the blocking agent being capable of reducing the adsorption by between about 10% to about 99% as determined by a standard adsorption assay.

13. The method of claim 12, wherein the blocking agent is a hexamethonium salt represented by the following formula:

$$[(CH_3)_3N^+(CH_2)_6N^+(CH_3)_3]2X^-$$

wherein X is a counter-ion.

14. The method of claim 13, wherein the hexamethonium salt comprises a halide.

15. The method of claim 14, wherein the hexamethonium salt is hexamethonium bromide (HMB).

16. The method of claim 1, wherein the blocking agent is a salt of tetramethyl ammonium, tetraethyl ammonium, tetrapropylammonium, trimethylethyl ammonium or triethylpropyl ammonium.

17. The method of claim 16, wherein the blocking agent comprises at least one halide.

18. The method of claim 17, wherein the halide is bromide or chloride.

19. The method of claim 1, wherein the blocking agent is a salt of N,N"-trimethyl-N'-dimethyl-bishexamethylene-triammonium, ethylenebis(trimethylammonium), propylenebis(trimethylammonium), butylenebis (trimethylammonium), pentamethylenebis (timethylammonium), or heptamethylenebis (trimethylammonium).

20. The method of claim 19, wherein the blocking agent comprises at least one halide.

21. The method of claim 20, wherein the halide is bromide or chloride.

22. The method of claim 1, wherein the blocking agent is a choline salt.

23. The method of claim 22, wherein the choline salt comprises at least one halide.

24. The method of claim 23, wherein the halide is bromide or chloride.

25. The method of claim 1, wherein the blocking agent is provided as a solid.

26. A method of reducing adsorption of an aminoglycoside to a glass or plastic surface, the method comprising combining the aminoglycoside with one or more hexamethonium salts in an amount sufficient to reduce the adsorption by between about 10% to about 99% as determined by a standard adsorption assay.

27. The method of claim 26, wherein the aminoglycoside is present in a sample to be assayed and is present covalently linked to a signaling molecule.

28. The method of claim 27, wherein the signaling molecule is a fluorophore or a chemiluminescent molecule.

29. The method of claim 28, wherein the fluorophore is fluorescein.

30. The method of claim 29, wherein the signaling molecule is an enzyme capable of generating a detectable molecule.

31. The method of claim 30, wherein the aminoglycoside is gentimicin, netilmicin, tobramycin, vancomycin or amikacin.

32. The method of claim 31, wherein the hexamethonium salts are hexamethonium halide salts provided in an amount between about 0.01% to about 10% (w/v) in the method.

33. The method of claim 32, wherein at least one of the hexamethonium halide salts is hexamethonium bromide (HMB) provided in a amount sufficient to provide between about 0.1% to about 5% (w/v) in the method.

34. An immunological assay for detecting at least one aminoglycoside in a sample, wherein the assay is carried out in a vessel comprising a negatively charged surface, the assay comprising the steps of:
   a) combining with the sample at least one hexamethonium halide salt in an amount sufficient to reduce adsorption of the aminoglycoside to the vessel,
   b) performing the immunological assay with the sample; and
   c) detecting the aminoglycoside in the sample.

35. The assay of claim 34, wherein the aminoglycoside is gentamicin and the hexamethonium halide salt is hexamethonium bromide (HMB) provided in an amount sufficient to provide in the method between about 0.01% to about 10% (w/v) of the salt.

36. A kit for detecting at least one aminoglycoside in a sample, the kit comprising a calibrator comprising one or more aqueous buffers comprising a known amount of the aminoglycoside, a conjugate (tracer) comprising a signaling molecule comprising glucose 6-phosphate dehydrogenase covalently linked to the aminoglycoside, an antibody capable of specifically binding the aminoglycoside, and at least one hexamethonium halide salt.

37. The kit of claim 36, wherein the aminoglycoside is gentamicin and the hexamethonium halide salt is hexamethonium bromide (HMB) in an amount between about 0.1% to about 0.5% (w/v) of the HMB.

38. The assay of claim 34, wherein the aminoglycoside is tobramycin, kanamycin, amikacin or vancomycin, and the hexamethonium halide salt is hexamethonium bromide (HMB) provided in an amount sufficient to provide in the assay between about 0.01% to about 10% (w/v) of the salt.

* * * * *